(12) United States Patent
Hoffmann

(10) Patent No.: US 7,519,162 B2
(45) Date of Patent: Apr. 14, 2009

(54) LIFTING DRIVE FOR A RADIATION FILTER IN A MAMMOGRAPHY DEVICE

(75) Inventor: Norbert Hoffmann, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 40 days.

(21) Appl. No.: 11/729,220

(22) Filed: Mar. 28, 2007

(65) Prior Publication Data

US 2008/0037704 A1   Feb. 14, 2008

(30) Foreign Application Priority Data

Apr. 12, 2006   (DE) ...................... 10 2006 017 310

(51) Int. Cl.
*G21K 3/00* (2006.01)
*G21K 1/10* (2006.01)

(52) U.S. Cl. ...................... 378/155; 378/156
(58) Field of Classification Search ............ 378/37, 378/155–158, 160
See application file for complete search history.

(56) References Cited

U.S. PATENT DOCUMENTS

| 2,864,004 | A | * | 12/1958 | Nemet et al. | ............ | 378/155 |
| 2,938,120 | A | * | 5/1960 | Forsyth | ............ | 378/155 |
| 4,071,767 | A | * | 1/1978 | Pury et al. | ............ | 378/176 |
| 4,105,920 | A | * | 8/1978 | Pury et al. | ............ | 378/91 |
| 4,542,521 | A | * | 9/1985 | Hahn et al. | ............ | 378/155 |
| 4,646,340 | A | * | 2/1987 | Bauer | ............ | 378/155 |
| 4,760,589 | A | * | 7/1988 | Siczek | ............ | 378/155 |
| 5,373,546 | A | * | 12/1994 | Holzermer | ............ | 378/157 |
| 6,862,340 | B2 | * | 3/2005 | Wurzer | ............ | 378/157 |
| 7,072,447 | B2 | * | 7/2006 | Graf et al. | ............ | 378/156 |
| 7,116,758 | B2 | * | 10/2006 | McKenna | ............ | 378/155 |
| 7,260,183 | B2 | * | 8/2007 | Yuan et al. | ............ | 378/158 |

FOREIGN PATENT DOCUMENTS

DE   33 16 003 A1   11/1984
DE   3316003 A1    11/1984

OTHER PUBLICATIONS

German Office Action for DE 10 2006 017 310.4-35 dated Jan. 9, 2007 and English translation.

* cited by examiner

*Primary Examiner*—Edward J Glick
*Assistant Examiner*—Thomas R Artman
(74) *Attorney, Agent, or Firm*—Brinks, Hofer, Gilson & Lione

(57) ABSTRACT

A lifting drive for a radiation filter in a mammography device is provided. The lifting drive includes a recording apparatus that accommodates the radiation filter. The recording apparatus is embodied so that the radiation filter is operatively supported to allow movement for executing a lifting movement in at least one lifting direction. A first drive element is operable to create a drive movement. A first movement transmission element is operable to transmit the drive movement to the recording apparatus. The recording apparatus is operable to convert the drive movement into the lifting movement. A shape of the first movement transmission element is operable to be changed, so that the drive movement is able to be transmitted over different paths.

18 Claims, 6 Drawing Sheets

LIFTING DRIVE FOR A RADIATION FILTER IN A MAMMOGRAPHY DEVICE

This patent document also claims the benefit of DE 10 2006 017 310.4, filed Apr. 12, 2006, which is also hereby incorporated by reference.

BACKGROUND

The present embodiments relate to a lifting drive for a radiation filter in a mammography device. The present embodiments also relate to a mammography device with a lifting drive.

Mammography devices may be used for fluoroscopy of an object to be examined, for example, a female breast. Mammography devices may feature a radiographic source and a radiation detector. The object to be examined is positioned between the radiographic source and the detector. Scattered radiation is predominantly caused by deflection of the examination rays in the x-rayed object under examination. Scattered radiation is especially problematic when x-raying thicker objects. To reduce the radiation scattering at the detector, an anti-scatter grid is usually arranged behind the object under examination and in front of the detector.

Anti-scatter grids may cause stripes or grids of noise on the examination image recorded in the detector. To reduce or eliminate these disturbance stripes, the anti-scatter grid is agitated slightly during the examination.

DE 3316003 A1 discloses a device for rectifying radiation scatter with an anti-scatter grid. The anti-scatter grid is moved back and forth once by a drive element as an image is recorded. A drive movement is created in a drive motor and converted via a fixed gear into an oscillating lifting movement of the anti-scatter grid.

SUMMARY

The present embodiments may obviate one or more of the drawbacks or limitations inherent in the related art. For example, in one embodiment, a lifting drive for a radiation filter in a mammography device is provided, and a mammography device provides greater design scope for the arrangement of components of the lifting drive or the components of the mammography device.

In one embodiment, a lifting drive is suitable and/or embodied for a radiation filter in a mammography device. The radiation filter is embodied as an anti-scatter grid and/or as an arrangement of a number of anti-scatter grids and/or as an x-ray grid. The radiation filter complies with the characteristic values in the required framework of DIN Standard 6826. In an alternative embodiment, the lifting drive may be used in other, especially medical, investigation devices in which a radiation filter is moved.

In one embodiment, the lifting drive includes a recording apparatus embodied to accommodate the radiation filter. When an examination is being undertaken, especially when an examination image is being recorded, the recording apparatus is arranged so that it is stationary, especially stationary relative to the mammography device and/or examination device.

The mechanical design of the recording apparatus allows the radiation filter to perform a lifting movement in at least one lifting direction relative to the recording apparatus and/or to the detector. The lifting direction is parallel or coplanar to the plane formed by the entry surface and/or the exit surface for the directed examination radiation of the radiation filter. In one embodiment, this involves a linear lifting movement. Alternatively a lifting movement with a curved movement track can also be provided.

The lifting drive includes a first drive apparatus that creates the drive movement. In one embodiment, the drive movement is an oscillating movement. In other embodiments, the drive movement may be a sine-wave drive movement or a saw tooth wave drive movement. In one embodiment, oscillating drive movements are used where the sum of the speed over time is constant and/or essentially constant. The drive apparatus may be a drive unit, which with the aid of a link apparatus, creates from a sine wave movement a linear saw tooth wave movement as the drive movement.

A first movement transmission element is provided. The first movement transmission element transmits the drive movement to the recording apparatus. The first movement transmission element is connected serially in the transmission. The recording apparatus converts the drive movement into the lifting movement.

The first movement transmission element may change its shape and can do this in such a way that the drive movement is transmitted over different curved paths.

The drive element can be placed at any given location. The drive movement is able to be transmitted from any given location via the movement transmission element to the recording apparatus. The drive element does not have to be arranged directly in the recording apparatus or have the element rigidly coupled to the recording apparatus.

In one embodiment, the first movement transmission element is reversible, elastically bendable, and/or plastically bendable. The movement transmission element is resistant to bending or is to be slack. In another embodiment, the first movement transmission element is constructed from individual chain elements.

In one embodiment, the first movement transmission element is a cable pull. The first movement transmission may be a Bowden cable. The Bowden cable includes an internal steel wire or a wire cable. The internal steel wire or wire cable can be laid in a flexible sleeve. The sleeve may be covered with plastic or textile. The sleeve may be a tightly wound, compression-proof wire spiral.

In another embodiment, the first movement transmission element is a hydraulic and/or pneumatic line. The drive movement is implemented pneumatically and/or hydraulically.

Depending on how the movement transmission element is implemented, the first movement transmission element is embodied for transmission of tensile and/or compression forces. The movement transmission element may be embodied for transmission of forces in both directions. The lifting movement is easy to create.

In one embodiment, the movement transmission element forces are only transmitted in one direction. The movement transmission element forces are either tensile forces or compression forces. A second movement transmission element may be provided. The second movement transmission element may be embodied to reset the first movement transmission element. The first and also second movement transmission elements may be embodied as cable pulls, especially Bowden cables.

In one embodiment, a counter force apparatus is arranged in the recording apparatus. The counter force apparatus works against the force or movement transmitted in the first and/or second movement transmission element. The counter force apparatus is a tensile and/or compression spring arrangement.

The combinations of actions able to be implemented include:

| Lifting movement in lifting direction | Resetting |
|---|---|
| A) | |
| Tensile force (compression force) via first movement transmission element | Compression force (tensile force) via first movement transmission element |
| B) | |
| Tensile force (compression force) via first movement transmission element | Tensile force (compression force) or compression force (tensile force) via second movement transmission element |
| C) | |
| Tensile force (compression force) via first movement transmission element | Tensile force (compression force) or compression force (tensile force) via counter force apparatus |

The recording apparatus together with the inserted radiation filter can be moved in such a way that examinations can be undertaken without this radiation filter. The recording apparatus is moved from an examination position into a rest position. The radiation filter is embodied so that it can be moved out of the x-ray recording area.

When the recording technology is changed, no major conversion measures are required at the examination device, especially at the mammography device. Such conversion work is for example usually necessary if, instead of a digital detector with radiation filter, a stereotaxy examination with an additional CCD camera or a tomosynthetic examination is to be performed.

The lifting drive with the carriage may include a few or all of the previously described features.

In one embodiment, the lifting drive is equipped with a second drive apparatus that is embodied and/or arranged to move the carriage.

The second drive apparatus is an electric motor that moves the carriage using a toothed bar or a toothed belt. The carriage is guided on precision shafts with slide bearings or similar, especially so that a play-free or almost play-free guidance is guaranteed. In alternative embodiments, miniature linear guides are used to guide the carriage.

The transfer of the recording apparatus from the examination position to the rest position is a deactivation of the radiation filter or of the grid.

In one embodiment, the carriage and/or the recording apparatus are arranged to allow movement relative to the first and/or the second drive apparatus. The relative movement to the first recording apparatus is only achieved by the drive movement that is transmitted via the deformable movement transmission element. The carriage can be implemented together with the recording apparatus in a very light or filigree construction since the drive apparatus is not transported on the carriage. The first drive element for the lifting movement of the radiation filter can be placed at almost any given position. From this almost any given position, the drive movement generated is transmitted via the movement transmission element to the radiation filter.

In one embodiment, a mammography device includes a lifting drive as described above with the radiation filter as an anti-scatter grid and/or x-ray grid.

In one embodiment, the deactivation of the radiation filter is controlled, for example, by a simple program selection and is able to be initiated by software. The mammography device is able to be operated with a high level of automation, since the operator does not have to make any manual and/or mechanical settings in advance in order to execute a specific recording technology.

DETAILED DESCRIPTION

Figure 1:
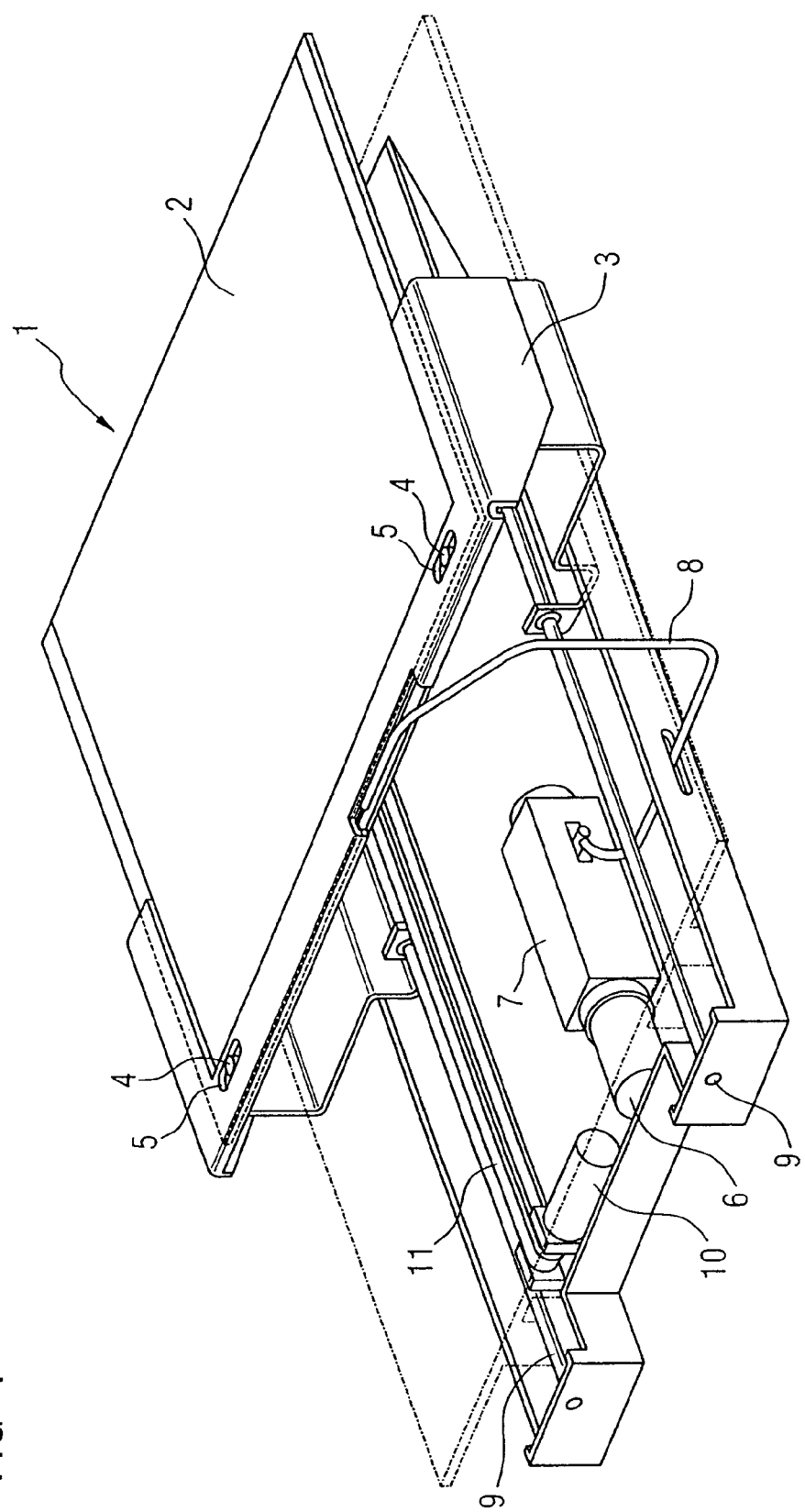
FIG. 1 is a three-dimensional side view of one exemplary embodiment of a lifting drive seen at an angle from above, FIG. 2 the lifting drive in FIG. 1, in a schematic three-dimensional front view from an oblique angle, FIG. 3 the lifting drive in FIG. 1, in a schematic three-dimensional view from above, FIG. 4 the lifting drive in FIG. 1, in a schematic three-dimensional side view with inserted detector, FIG. 5 the lifting drive in FIG. 1, in a similar view to that shown in FIG. 1 with activated anti-scatter grid, and FIG. 6 the lifting drive in FIG. 1, shown in the same view as in FIG. 5 with deactivated anti-scatter grid.

FIG. 1 shows a lifting drive 1 for an anti-scatter grid 2 which is supported to allow movement in a recording apparatus 3. The recording apparatus 3 is embodied as a grid plate, especially as a plate made from sheet metal. The anti-scatter grid 2 is a slatted shutter or a two-dimensional grid with a honeycomb or cross structure.

To move the anti-scatter grid 2 during the examination, especially to avoid noise stripes or other artifacts, two guide nipples 4 are provided in the recording apparatus 3. The two guide nipples 4 may be provided on the grid plate. The two guide nipples 4 engage in two longitudinal holes of the anti-scatter grid 2 or a frame construction for fixed support of the anti-scatter grid 2. The anti-scatter grid 2 is able to move in the direction of extension of the longitudinal holes 5 oscillating back and forth relative to the recording apparatus 3.

To generate this relative movement between the anti-scatter grid 2 and the recording apparatus 3, a first electric motor 6 is provided which uses a linkage apparatus 7 to transform the sine-wave motor movement of the first electric motor 6 into a linear saw tooth movement. This drive movement generated by the first electric motor 6 and transformed by the linkage apparatus 7 is transmitted via a flexible movement transmission element in the form of a Bowden cable 8 to the recording apparatus 3. The Bowden cable 8 has a sleeve. One end of the Bowden cable 8 is fixed to the recording apparatus 3 and the other end is fixed to the linkage apparatus 7. One end may be fixed to the grid plate. The linear saw tooth movement is transferred via the Bowden cable 8 to the recording apparatus 3. In one embodiment, the steel cable guided in the sleeve of the Bowden cable 8 is permanently coupled to the anti-scatter grid 2. The anti-scatter grid 2 can be moved back and forth by the movement of the steel cable in the Bowden cable 8 along the longitudinal holes 5.

Because of the flexibility of the Bowden cable 8, it is better able to transfer tensile forces than compressive forces. To guarantee a resetting of the anti-scatter grid 2 in the compression direction of the Bowden cable, optional compression or tensile springs are provided that are arranged so that they act against the compression force or the tensile movement of the Bowden cable 8, especially of the steel cable in the Bowden cable 8.

In one embodiment, another Bowden cable which is arranged to run in the opposite direction to the Bowden cable 8 is used. The oscillating movement of the anti-scatter grid 2 is created by an alternating transmission of tensile forces by the Bowden cables.

The recording apparatus 3 is embodied in the lifting drive 1 as a moveable carriage. The recording apparatus 3 is guided captively on two precision shafts 9 that are arranged in parallel to each other. The recording apparatus 3 and the anti-scatter grid 2 are moved sideways in one direction of movement so that the anti-scatter grid 2 is deactivated.

The anti-scatter grid 2 is deactivated when the anti-scatter grid 2 is withdrawn from a detector area. The amount of movement may be around the width of the anti-scatter grid 2 in the direction of movement. The recording apparatus 3 can be moved manually on the precision shafts 9 or by, as shown in FIG. 1-6, a second electric motor 10. The second electric motor 10 moves the recording apparatus 3 embodied as a carriage via a toothed belt 11.

The first electric motor 6, the link apparatus 7, and the second electric motor 10 are arranged below the precision shafts 9. The contours of these components do not interfere with the movement of the recording apparatus 3.

The recording apparatus 3 embodied as a carriage is moved in relation to the stationary components first electric motor 6, link device 7, and second electric motor 10. The flexible Bowden cable 8 makes it possible to execute the displacement movement without separating the movement transmission between the drive unit for the lifting movement, for example, first electric motor 6 and link device 7, and recording apparatus 3.

Figure 2:
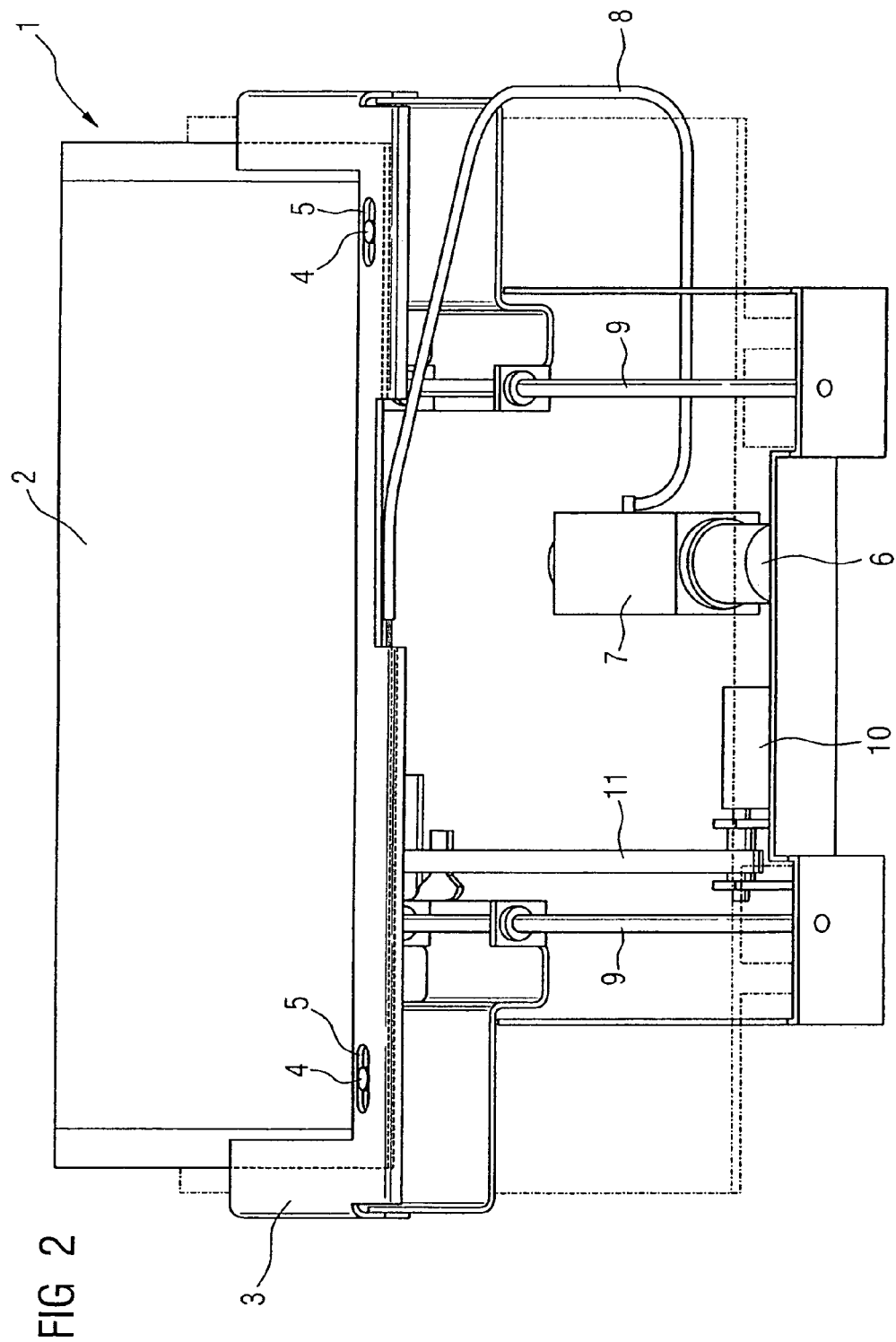
Figure 3:
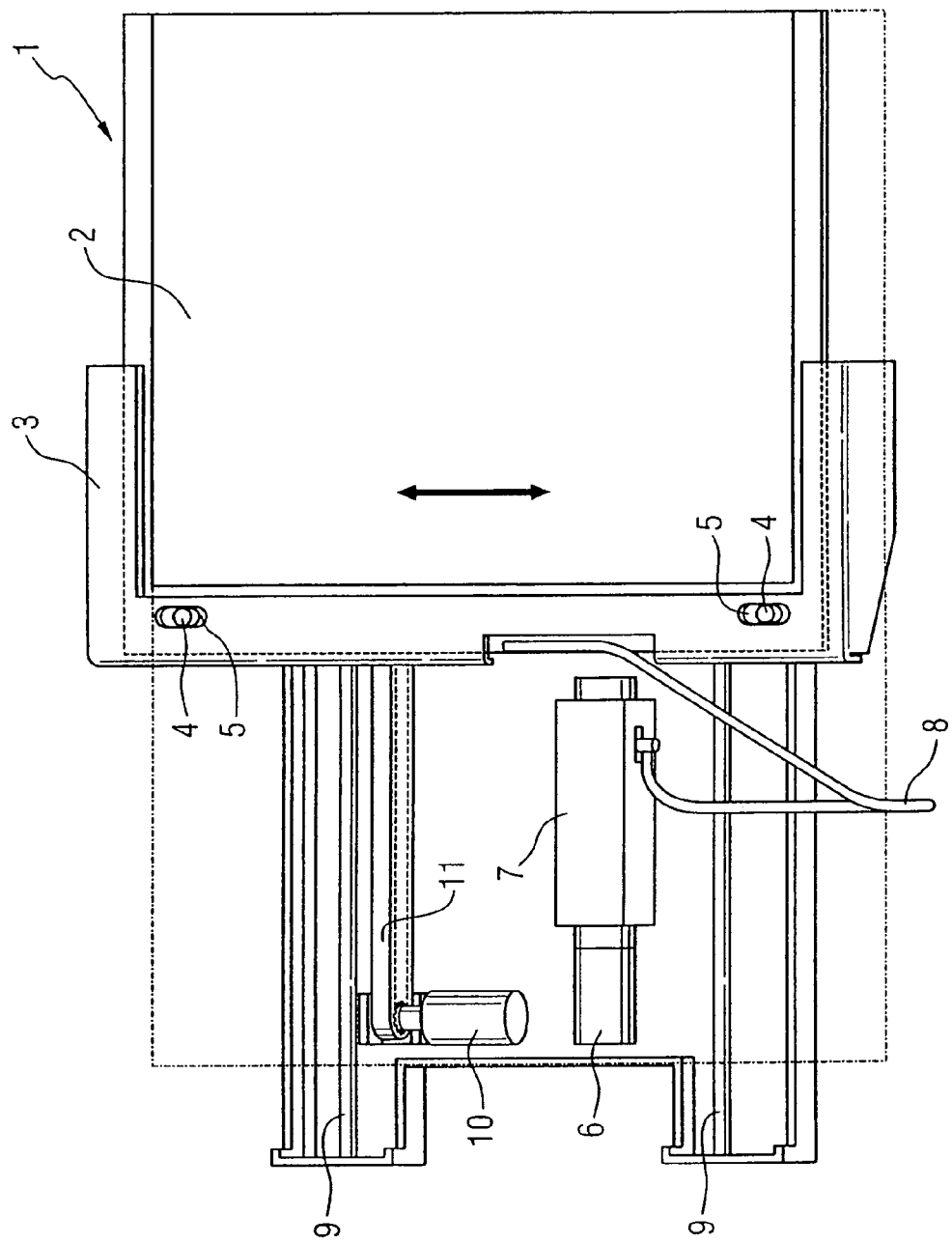

FIGS. 2 and 3 show the lifting drive 1. The direction of lift is indicated in FIG. 3 by a black double-ended arrow.

Figure 4:
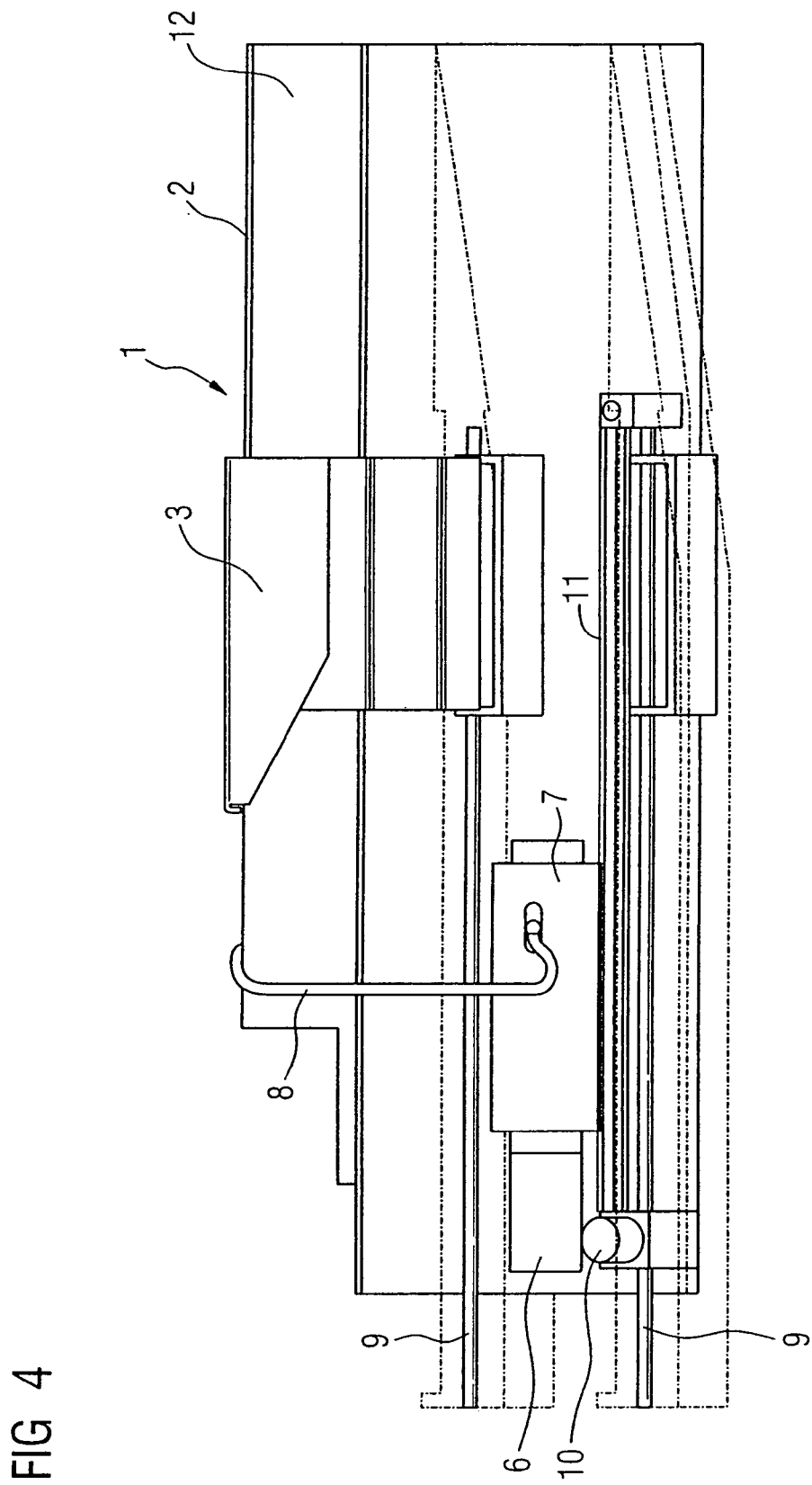

The recording apparatus 3 and the anti-scatter grid 2, as shown in FIG. 4, are in an end position on the right hand side. FIG. 4 shows a detector 12 for which the detection area is positioned below the anti-scatter grid 2. In the left end position of the recording apparatus 3, the detector 12 in the measurement or detector area is no longer covered by the anti-scatter grid 2. In this end position the anti-scatter grid 2 is deactivated.

Figure 5:
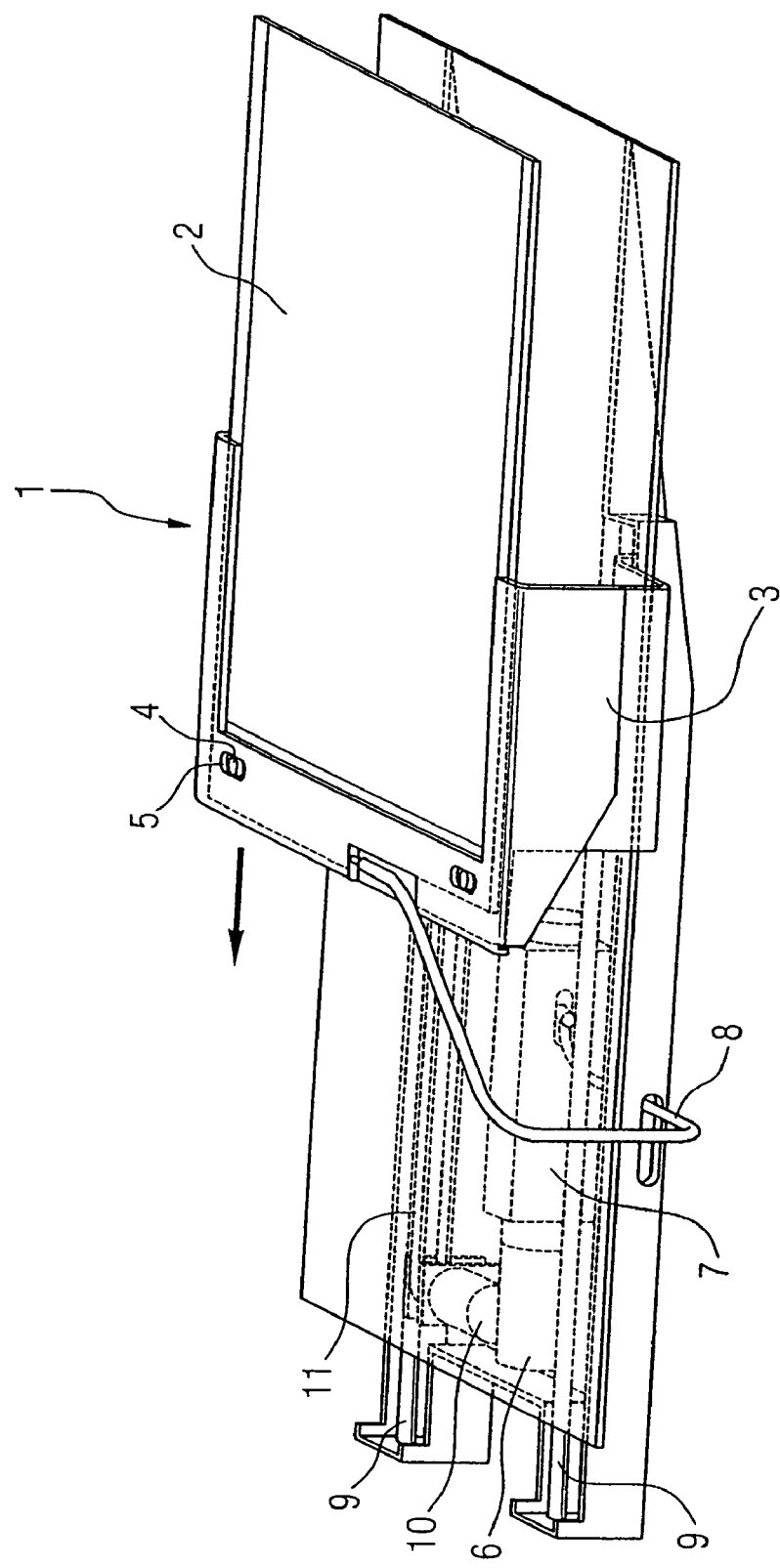
Figure 6:
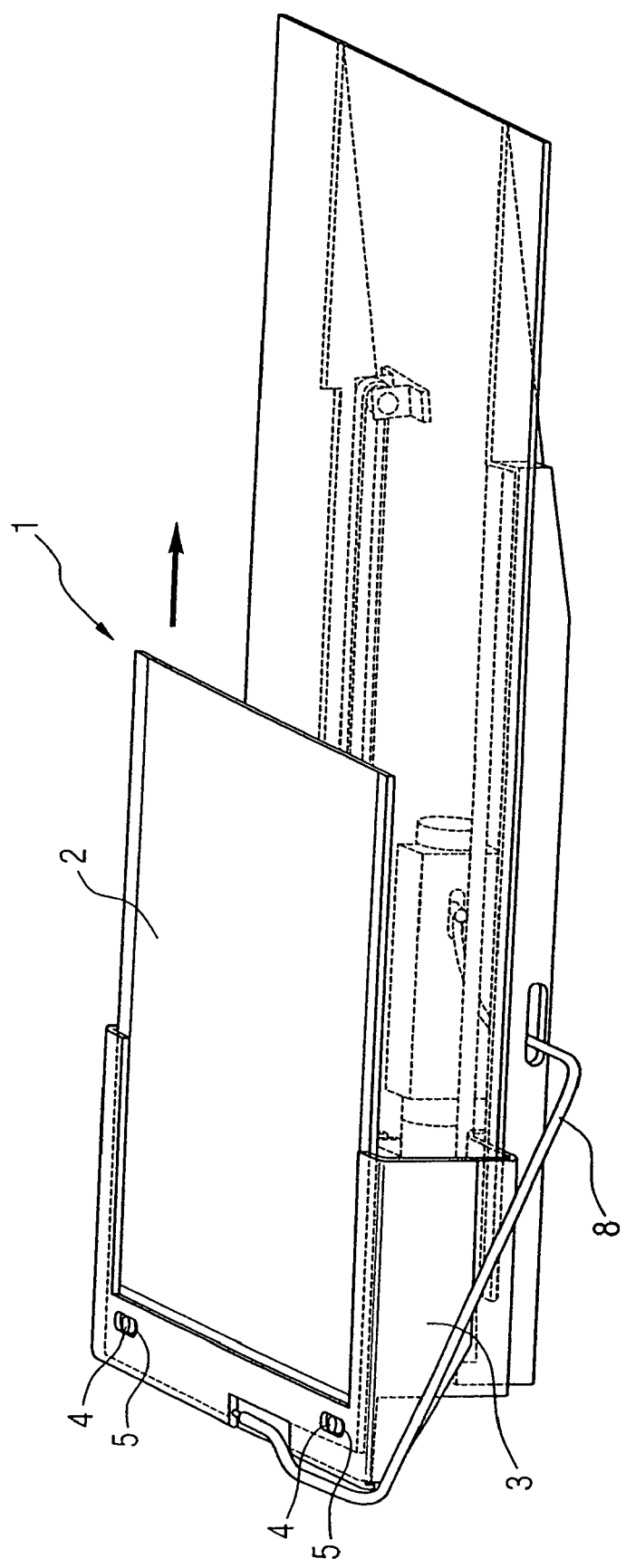

FIGS. 5 and 6 show the lifting drive 1 with an activated or with a deactivated anti-scatter grid 2. FIG. 5 shows the activated state. FIG. 6 shows the deactivated operating state.

As shown in FIGS. 5 and 6, a flexible movement transmission element such as the Bowden cable 8 is used. The Bowden cable 8 allows the drive unit for the lifting movement of the anti-scatter grid, for example, the first electric motor 6 and the link apparatus 7, to be positioned at any point independent of the recording apparatus 3.

A lifting drive 1 includes a drive unit, which is used for the lifting movement of the anti-scatter grid 2 that is arranged stationary in relation to the examination device, especially to the mammography device. The drive unit can remain in place both for an activated and also a deactivated anti-scatter grid 2 because of the connection between anti-scatter grid 2 or recording apparatus 3 and drive unit via the Bowden cable 8.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A lifting drive for a radiation filter in a mammography device,
   the lifting drive comprising:
   a recording apparatus that accommodates the radiation filter, the recording apparatus being embodied so that the radiation filter is operatively supported to allow movement for executing a lifting movement in at least one lifting direction,
   a first drive that is operable to create a drive movement, and
   a first movement transmission for transmission of the drive movement to the recording apparatus, a first end of the first movement transmission is fixed to the recording apparatus and a second end of the first movement transmission is fixed to the first drive such that the recording apparatus is operable to convert the drive movement into the lifting movement,
   wherein a shape of the first movement transmission is operable to be changed, so that the drive movement is able to be transmitted over different paths.

2. The lifting drive as claimed in claim 1, wherein the first movement transmission is reversible, elastically bendable, plastically bendable, or any combination thereof.

3. The lifting drive as claimed in claim 1, wherein the first movement transmission is a Bowden cable.

4. The lifting drive as claimed in claim 1, wherein the first movement transmission is operable to transmit compression forces.

5. The lifting drive as claimed in claim 1, comprising a second movement transmission, the second movement transmission being operable to reset the first movement transmission.

6. The lifting drive as claimed in claim 5, wherein the recording apparatus includes a counter force apparatus, the counter force apparatus being operable to act against the force or movement transmitted by the first movement transmission, second movement transmission, or both the first and second transmissions.

7. The lifting drive as claimed in claim 6, wherein the counter force apparatus includes a tensile or compression spring facility.

8. The lifting drive as claimed in claim 1, wherein the recording apparatus is located on a carriage, the carriage being operable to allow a displacement of the recording apparatus.

9. The lifting drive as claimed in claim 8, wherein a second drive is operable to allow the movement of the carriage.

10. Lifting drive as claimed in claim 8, wherein the carriage, the recording apparatus, or both are operable to allow movement relative to the first and/or the second drive element.

11. The lifting drive as claimed in claim 1, wherein the first movement transmission is a hydraulic line, pneumatic line, or both.

12. The lifting drive as claimed in claim 1, wherein the first movement transmission is operable to transmit tensile, compression, or both tensile and compression forces.

13. A mammography device comprising:
   a lifting drive that includes:
   a recording apparatus that accommodates a radiation filter, the recording apparatus being embodied so that the radiation filter is operatively supported to allow movement for executing a lifting movement in at least one lifting direction,
   a first drive that is operable to create a drive movement, and
   a first movement transmission for transmission of the drive movement to the recording apparatus, a first end of the first movement transmission is fixed to the recording apparatus and a second end of the first movement transmission is fixed to the first drive such that the recording apparatus is operable to convert the drive movement into the lifting movement, wherein a shape of the first movement transmission is operable to be changed, so that the drive movement is able to be transmitted over different paths, and wherein the radiation filter is an anti-scatter grid, x-ray grid, or both.

14. The mammography device as claimed in claim 13, wherein the first movement transmission is a Bowden cable.

15. The mammography device as claimed in claim 13, wherein the first movement transmission is operable to transmit tensile, compression, or both forces.

16. The mammography device as claimed in claim 13, comprising a second movement transmission, the second movement transmission being operable to reset the first movement transmission.

17. The mammography device as claimed in claim 16, wherein the recording apparatus includes a counter force apparatus, the counter force apparatus being operable to act against the force or movement transmitted by the first movement transmission, second movement transmission, or both the first and second transmissions.

18. The mammography device as claimed in claim 13, wherein the recording apparatus is located on a carriage, the carriage being operable to allow a displacement of the recording apparatus.

* * * * *